United States Patent [19]

Martin et al.

[11] Patent Number: 4,617,291

[45] Date of Patent: Oct. 14, 1986

[54] ANGIOTENSIN-CONVERTING ENZYME INHIBITING DIPEPTIDE DERIVATIVES

[75] Inventors: Tellis A. Martin; Terence M. Dolak, both of Evansville, Ind.

[73] Assignee: Mead Johnson & Company, Evansville, Ind.

[21] Appl. No.: 378,295

[22] Filed: May 14, 1982

[51] Int. Cl.[4] ............... A61K 37/43; C07K 5/06; C07C 101/44
[52] U.S. Cl. .................................. 514/19; 560/44; 560/457; 530/800; 562/457
[58] Field of Search ............... 424/177; 260/112.5 R; 548/492; 514/19; 560/44, 457

[56] References Cited

U.S. PATENT DOCUMENTS

| | | | |
|---|---|---|---|
| 4,303,583 | 12/1981 | Kim et al. | 548/492 |
| 4,344,949 | 8/1982 | Hoefle et al. | 424/258 |
| 4,404,206 | 9/1983 | Vincent et al. | 424/258 |

FOREIGN PATENT DOCUMENTS 2095682 10/1982 United Kingdom ......... 260/112.5 R

Primary Examiner—Delbert R. Phillips
Attorney, Agent, or Firm—Robert H. Uloth; Richard P. Ryan

[57] ABSTRACT

Dipeptides having the formula

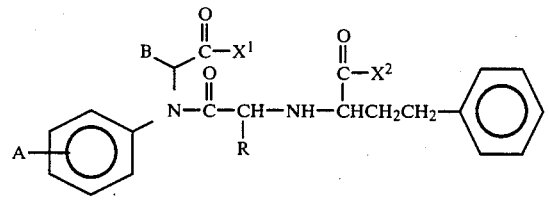

wherein A is halogen, hydrogen, lower alkyl, or lower alkoxy; B is hydrogen or lower alkyl, or A and B are taken together to form an ortho-methylene or ethylene bridge; R is hydrogen, lower alkyl, or phenylalkyl; and $X^1$ and $X^2$ are independently chosen from hydroxy or lower alkoxy; are inhibitors of angiotensin-converting enzyme and can be used for the treatment of hypertension in mammals.

5 Claims, No Drawings

ANGIOTENSIN-CONVERTING ENZYME INHIBITING DIPEPTIDE DERIVATIVES

BACKGROUND OF THE INVENTION

The literature is replete with disclosures of the inhibition of the conversion of angiotensin I into angiotensin II by amino acid and small peptide analogs. Considerable variation in the nature of the analog functionality and the specific amino acid residues seems allowable without loss of activity in inhibiting angiotensin converting enzyme. Early on, U.S. Pat. No. 3,832,337 issued Aug. 27, 1974 disclosed peptides and acylated peptides that blocked the conversion of angiotensin I into angiotensin II.

The most numerous group of compounds which have been disclosed to be inhibitors of angiotensin converting enzyme are the mercaptoacylamino acids of which captopril (D-(3-mercapto-2-methyl-1-oxopropyl)-L-proline) is the best known. Captopril is disclosed in U.S. Pat. No. 4,105,776, issued Aug, 8, 1978, and is now in use as a treatment for hypertension.

As an example of the structural diversity permissible, U.S. Pat. No. 4,256,761, issued Mar. 17, 1981, discloses the following structure

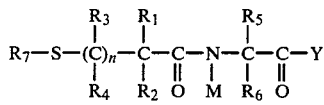

wherein $R_1$, $R_2$, $R_3$, $R_4$, $R_5$, and $R_6$ are hydrogen, alkyl, alkenyl, alkynyl, phenyl-alkyl, or cycloalkyl, n is an integer from 0 to 4 inclusive, M is alkenyl, alkynyl, cycloalkyl, cycloalkyl-alkyl, polycycloalkyl, polycyclo-alkyl-alkyl, aryl, aralkyl, heteroaryl, heteroaryl-alkyl, hetero-cycloalkyl, heterocycloalkyl-alkyl, alkoxyalkyl, alkylthioalkyl, alkylamino-alkyl, dialkylamino-alkyl, fused aryl-cycloalkyl, fused aryl-cycloalkyl-alkyl, fused heteroaryl-cycloalkyl, or fused heteroaryl-cycloalkyl-alkyl, Y is hydroxy, alkoxy, amino, or substituted amino, aminoalkanoyl, aryloxy, aminoalkoxy, or hydroxyalkoxy, and $R_7$ is hydrogen, alkanoyl, carboxylalkanoyl, hydroxy-alkanoyl, amino-alkanoyl, cyano, amidino, carbalkoxy, ZS, or

wherein Z is hydrogen, alkyl, hydroxyalkyl, aminoalkyl or the radical

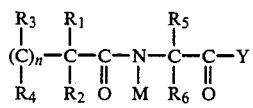

wherein $R_1$, $R_2$, $R_3$, $R_4$, $R_5$, $R_6$, n, M and Y are as described above.

Angiotensin converting enzyme inhibitors having a tripeptide structure are disclosed in U.S. Pat. No. 4,293,481, patented Oct. 6, 1981, and have the following formula

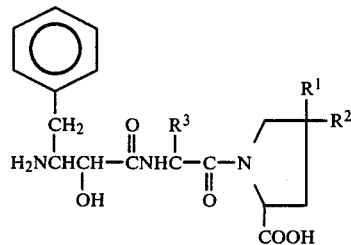

wherein $R^1$ and $R^2$ are selected from hydrogen or a variety of functional groups and $R^3$ is hydrogen, alkyl or trifluoromethyl.

The closest relevant art would be some dipeptide analogs which were originally reported by Patchett, et al at the 17th National Medicinal Chemistry Symposium, June 15-19, 1980 in Troy, N.Y. These compounds formed the basis for European Patent Application No. 79105015.6 by Merck and Co. which was published June 25, 1980. The general formula disclosed is

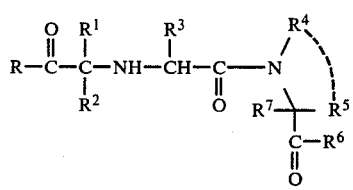

Merck Series of which one member, enalapril (MK-421) is currently being developed as a treatment for hypertension.

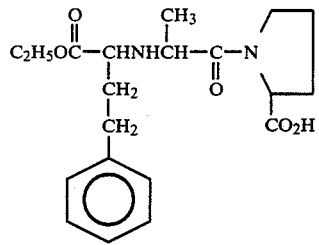

enalapril (MK-421)

The formula of compounds of the instant invention, shown as I,

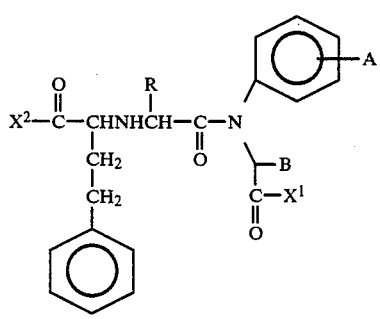

I can be distinguished from the general structure of the enalapril series by virtue of its phenyl substituent on the nitrogen atom of the glycine carboxy terminal amino acid residue. In the Merck & Company series of compounds $R_4$ is disclosed as being either hydrogen or alkyl.

SUMMARY OF THE INVENTION

This invention concerns a series of angiotensin-converting enzyme inhibitors having the general structural formula (I) and their non-toxic pharmaceutically acceptable salts and/or hydrates.

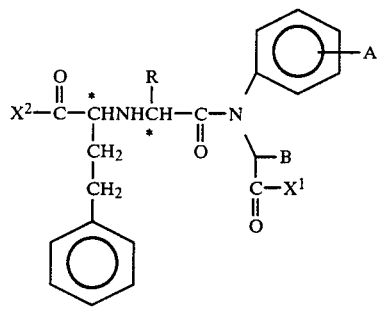

(I)

In the foregoing structural formula, A is halogen, hydrogen, lower ($C_1$ to $C_4$) alkyl or lower alkoxy; B is hydrogen or lower alkyl, or A and B are taken together to form an ortho-methylene or ethylene bridge; R is hydrogen, lower alkyl, or phenyl alkyl; and $X^1$ and $X^2$ are independently chosen from hydroxy or lower alkoxy.

The carbon atoms marked with an asterisk in formula I are asymmetric and can exist in the S or R configuration. The four possible stereoisomers (S,S; S,R; R,S; R,R) are encompassed by this invention.

These dipeptide derivatives of formula I inhibit the action of angiotensin-converting enzyme and are useful for lowering blood pressure.

DETAILED DESCRIPTION OF THE INVENTION

This invention in its broadest aspect relates to the dipeptide derivatives having formula I above and to salts and/or hydrates thereof, to compositions containing such compounds and to the method for using such compounds an antihypertensive agents.

The term "lower alkyl" as used in defining the symbols "A", "B", and "R" are straight or branched chain hydrocarbon radicals having up to four carbons with methyl and ethyl being most preferred. Similarly, the term "lower alkoxy", used in defining A, $X^1$ and $X^2$, refers to such lower alkyl groups attached to an oxygen. A and B may also be taken together to form an ortho-methylene or ethylene bridge, thereby producing indoline and tetrahydroquinoline moieties, respectively.

Preferred compounds of formula I are the alanine containing derivatives, i.e., R is methyl. Most preferred compounds comprise those in which A and B are hydrogen, $X^1$ is hydroxy, and $X^2$ is alkoxy, particularly ethoxy.

The asterisks in the above formula indicate centers of asymmetry in the molecule. These compounds can accordingly exist in stereoisomeric forms or as racemic mixtures thereof. All of these are within the scope of the invention. The synthesis described below can utilize an enantiomer or the racemic modification as starting materials. When the racemic starting material is used in the synthetic procedure, the stereoisomers obtained as products can be separated by conventional chromatographic or fractional crystallization methods.

The dipeptides of this invention can be prepared using as starting materials a compound having the formula II

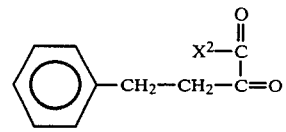

II wherein $X^2$ is not hydroxy but is otherwise as defined above; an amino acid having the formula III

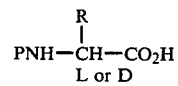

III

L or D wherein P is an acyl protecting group such as arylalkoxycarbonyl or alkoxycarbonyl, and L or D designates the configuration of the asymmetric carbon atom; and an N-phenyl amino acid having the formula IV

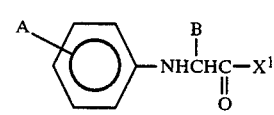

IV wherein A, B, and $X^1$ are as defined above except that $X^1$ is not hydroxy.

The synthesis of the dipeptides of this invention can be accomplished by first coupling the amino acids of formulas III and IV, removing the protecting group, and subsequently reacting the resulting dipeptide with a ketone of formula II in the presence of a reducing agent. Alternatively, the ketone (II) could be reacted with amino acid III (when P=hydrogen) and the resulting amino acid derivative then coupled with an amino acid of structure IV.

The coupling reactions utilized in these synthetic schemes can be accomplished using known amide bond forming procedures that are conventionally used in peptide syntheses. The reaction may be run in the presence of a coupling agent such as dicyclohexylcarbodiimide or an alkyl chloroformate, or the acid can be activated by forming, for example, its mixed anhydride, symmetrical anhydride, acid halide (preferably acid chloride) or acid ester, or by the use of Woodward reagent K (N-ethoxycarbonyl-2-ethoxy-1,2-dihydroquinoline) or the like. A review of these methods can be found in Methoden der Organischen Chemie (Houben-Weyl), Vol. XV, Part II, (1974).

The products of formula I can form basic salts with various inorganic and organic bases and these are also within the scope of this invention. Such salts might include ammonium salts; alkali metal salts, like sodium and potassium salts; alkaline earth metal salts like the calcium and magnesium salts; salts with organic bases, e.g., dicyclohexylamine salts, benzathine, N-methyl-D-glucamine, hydrobamine salts, and salts with amino acids like arginine, lysine, and the like. The non-toxic, physiologically acceptable salts are preferred, although other salts may be useful in isolating or purifying the dipeptide product. These salts can be formed using conventional techniques which are well known to any practitioner of the chemical art.

The dipeptides of formula I, and salts thereof, are useful as hypotensive agents. They inhibit the conversion of the decapeptide angiotensin I to to octapeptide angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin-converting enzyme (ACE) to angiotensin II. The latter is an active pressor substance which has been implicated as a causative agent in various forms of hypertension in various mammalian species, e.g., rats and dogs. The dipeptides of this invention intervene in the angiotensinogen→(renin)-→angiotensin I→(ACE)→angiotensin II sequence by inhibiting angiotensin-converting enzyme and reducing or eliminating the formation of the pressor substance angiotensin II. Thus, by the administration of a composition containing at least one of the dipeptides of this invention, angiotensin dependent hypertension in a species of mammals may be alleviated. A single dose, or preferably two to four divided daily doses, provided on a basis of about 0.1 to 100 mg per kg of body weight per day, preferably about 1 to 25 mg per kg of body weight per day, may be appropriate to reduce blood pressure. The composition is preferably administered orally, but parenteral routes such as the subcutaneous, intramuscular, intravenous or intraperitoneal routes can also be employed.

The dipeptides of this invention may also be formulated in combination with a diuretic for the treatment of hypertension. A combination product comprising a dipeptide of this invention and a diuretic can be administered in an effective amount which comprises a total daily dosage of about 30 to 600 mg, preferably about 30 to 350 mg of a compound of this invention and about 15 to 300 mg, preferably about 15 to 200 mg of the diuretic, to a mammalian species to be treated. Some examples of diuretics contemplated for use in combination with a dipeptide of this invention would be the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

These formula I dipeptides may be formulated for use in the reduction of blood pressure in compositions such as tablets, capsules, or elixirs for oral administration, or in sterile solutions or suspensions for parenteral administration. About 10 to 500 mg of at least one of the dipeptides of formula I is compounded with a physiologically acceptable vehicle, carrier, excipient, binder, preservative, stabilizer, flavor, etc., in a unit dosage form as called for by accepted pharmaceutical practice. The amount of material of the instant invention in these compositions or preparations is such that a suitable dosage in the range indicated is obtained.

DESCRIPTION OF SPECIFIC EMBODIMENTS

The compounds which constitute this invention and their methods of preparation will appear more fully from a consideration of the following synthetic scheme and examples which are given for the purpose of illustration only and are not to be construed as limiting the invention in sphere or scope. In examples which follow, used to illustrate the synthetic processes, temperatures are expressed in degrees celsius (°). Melting points are uncorrected. The proton nuclear magnetic resonance (NMR) spectral characteristics refer to chemical shifts (δ) expressed as parts per million (ppm) versus tetramethylsilane (TMS) as reference standard. The relative area reported for the various shifts in the H NMR spectral data corresponds the the number of hydrogen atoms of a particular functional type in the molecule. The nature of the shifts as to multiplicity is reported as broad singlet (bs), singlet (s), multiplet (m), doublet (d), or quartet (q). Abbreviations employed are DMSO-$d_6$ (deuterodimethylsulfoxide), $CDCl_3$ (deuterochloroform), and are otherwise conventional. The infrared (IR) spectral descriptions include only absorption wave numbers ($cm^{-1}$) having functional group identification value. The IR determinations were employed using potassium bromide (KBr) as diluent. The elemental analyses are reported as percent by weight.

EXAMPLE SYNTHETIC SCHEME

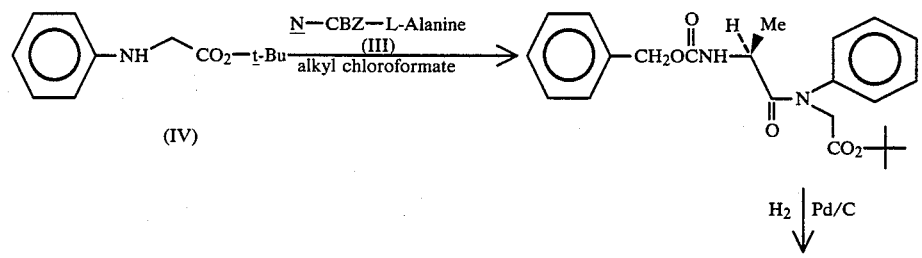

-continued
EXAMPLE SYNTHETIC SCHEME

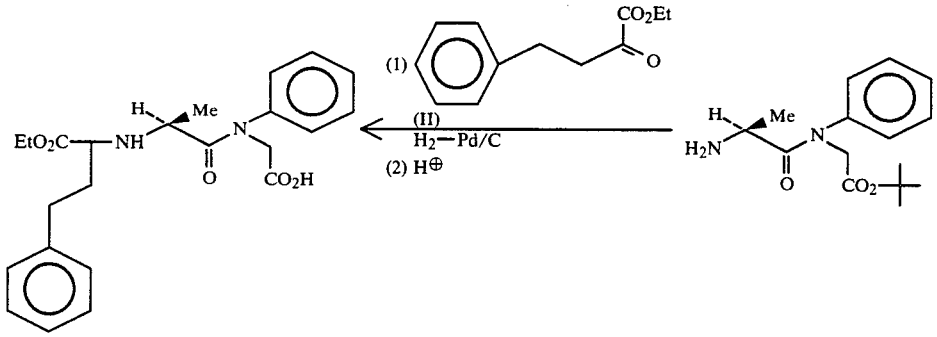

EXAMPLE 1

(S,S)-N-[1-(Ethoxycarbonyl)-3-phenyl-propyl]alanyl-N-phenylglycine Hydrate (I)

(a) 2-Oxo-4-phenylbutyric Acid Ethyl Ester (II).

3-Phenylpropionaldehyde (0.40 mole) was added dropwise to a solution of sodium bisulfite (0.80 mole) in 240 mL water and 50 mL 95% ethanol at room temperature over a 30 min period. A solution of sodium cyanide (0.40 mole) in 60 mL water was added dropwise to the stirred white suspension over a 20 min period at room temperature. After continuing stirring for an additional 2 hrs, the reaction mixture was extracted with ether (4×250 mL). The extracts were combined, dried (MgSO$_4$) and concentrated in vacuo to give 30.4 g (47%) of 2-hydroxy-4-phenylbutyronitrile as a viscous pale yellow oil.

This yellow oil was combined with ethanol (0.28 mole) in 210 mL ether and the resulting solution was cooled to 0° C. and then saturated with HCl gas for 1 hr. The reaction mixture was then stoppered and kept below 4° C. for a 16 hr period. Concentration in vacuo yielded a solid residue which was triturated in 300 mL ether and filtered to give 40.8 g (90% yield) of ethyl 2-hydroxy-4-phenylbutyroiminocarboxylate hydrochloride as a white solid, m.p. 90°–97° C. (dec).

This hydrochloride salt was stirred into 450 mL water at room temperature and stirring continued for 4 hr during which time an oily layer separated. The resultant oily mixture was extracted with ether (2×200 mL) and the ether extracts dried (MgSO$_4$) and concentrated in vacuo to afford 34.0 g (97% yield) of ethyl 2-hydroxy-4-phenylbutyrate as a pale yellow oil.

A 0.048 mole portion of this yellow oil was dissolved in 100 mL acetone and this solution was stirred at 10°–15° C. while 18 mL of Jones reagent (CrO$_3$—H$_2$SO$_4$) was added dropwise. After completion of the addition, the resulting green suspension was stirred for an additional hour while being kept in the 10°–15° C. range and then excess isopropyl alcohol (2 mL) was added to decompose the excess oxidizing agent. The suspension was filtered and the precipitate washed with fresh acetone. The filtrate and acetone washes were combined and concentrated in vacuo to give a residue which was taken up in 150 mL ether. This ether solution was washed with water (2×50 mL), dried (MgSO$_4$) and concentrated in vacuo affording 9.4 g (95% yield) of II as a yellow oil. Intermediate product II may be used in reaction (d) without further purification.

(b) t-Butyl N-Phenylglycinate (IV).

A solution consisting of 15 g of trifluoroacetanilide (previously prepared by the reaction of trifluoroacetic anhydride with aniline in ethyl ether at about 0° over a 30 min period) in 20 mL dry THF was added dropwise to a stirred suspension of hexane-washed NaH (4.19 g) in 100 mL THF at room temperature over a 1 hr period. The mixture was stirred for an additional 30 min following which t-butyl bromoacetate (16.2 g; 0.83 mole) was added to this reaction mixture. After further stirring for 16 hr, the reaction mixture was concentrated in vacuo to a residue which was then suspended in 200 mL ether and filtered using Celite or a comparable filter aid. The filtrate was concentrated in vacuo to a residual oil which was dried under high vacuum (0.02 mm Hg) for 16 hr to yield, in essentially quantitative yield, 24.1 g of an orange oil, t-butyl N-phenyl-N-trifluoroacetylglycinate.

This oily intermediate was combined with 150 mL 1N NaOH solution in 150 mL THF and heated at 50° C. for 90 min. The THF was removed in vacuo and the resulting aqueous oil mixture was extracted with three 150 mL portions of CHCl$_3$. These CHCl$_3$ extracts were combined, dried (MgSO$_4$) and concentrated to a residue which was chromatographed on silica gel eluting with hexane-EtOAC (19:1) to give 15.2 g (93% yield) of product in the form of a pale yellow oil which can be used without purification in reaction (c).

(c) t-Butyl N-S-Alanyl-N-phenylglycinate.

To a chilled (−15° C.) solution of N-carbobenzyloxy-L-alanine, III, (16.8 g; 0.75 mole) in 400 mL dry tetrahydrofuran (THF) was added sequentially: N-methylmorpholine (8.3 mL; 0.75 mole); i-butyl chloroformate (9.8 mL; 0.75 mole); and t-butyl N-phenylglycinate, IV, (15.0 g; 0.75 mole). This reaction mixture was allowed to gradually warm to room temperature while being stirred. After 72 hrs, the reaction mixture was concentrated in vacuo to a residue which was dissolved in 500 mL ethyl acetate and washed sequentially with saturated NaHCO$_3$ solution, 0.5N HCl solution, and H$_2$O. The ethyl acetate portion was dried (MgSO$_4$) and concentrated in vacuo to a residue which was chromatographed on silica gel eluting with CCl$_4$-EtOAC (9:1) affording 22.5 g (72.5%) of a yellow oil, $[\alpha]^D_{25} = +75.1°$ (C=2, CHCl$_3$).

This yellow oil was treated with 5–10% palladium-on-carbon catalyst (5.0 g) and glacial acetic acid (25 mL) in absolute ethanol (225 mL). This mixture was hydrogenated at 50 psi at room temperature for 16 hr. The catalyst was removed by filtration and the filtrate was concentrated in vacuo to a residue which was dissolved in CHCl$_3$ (500 mL) and washed with saturated NaHCO$_3$ solution. The chloroform portion was dried (d) (S,S)-N-[1-(Ethoxycarbonyl)-3-phenylpropyl]alanyl-N-phenylglycine Hydrate (I).

A mixture of 2-oxo-4-phenylbutyric acid ethyl ester, II, (4.8 g; 0.23 mole) and t-butyl N-S-alanyl-N-phenylglycinate (5.0 g; 0.18 mole) in hexane-ethyl acetate (2:1; 45 mL) was stirred at room temperature for 5 hr. A 10% Pd-on-C catalyst (5.0 g) was added under a nitrogen atmosphere and the resulting mixture hydrogenated at atmospheric pressure and room temperature for 48 hr. at which point one equivalent of hydrogen had been absorbed. The catalyst was removed by filtration. The filtrate was concentrated in vacuo and the resulting residue was chromatographed on a silica gel column (600 g of 250-400 mesh silica gel) eluting with hexane-ether (2:1). This chromatographic process was run under medium pressure of 20 to 40 psi and this afforded separation of the R,S- and the S,S-isomers. The isomer eluting first from the column was assigned the R,S-structure and the second product eluted, which was the major product, was assigned the S,S-structure.

This isomer was dissolved in $CF_3CO_2H$ (10 mL) and stirred for 2 hr at room temperature. The solution was then concentrated in vacuo and the residue dissolved in saturated $NaHCO_3$ solution. Dowex 50 (40 mL of the acid form) and ethanol (10 mL) were added giving a homogenous suspension which was then poured onto a column of 25 mL of Dowex 50, washed with 100 mL of 50% ethanol, then 100 mL of water, and finally 600 mL of a 2% pyridine in water solution. The pyridine solution eluent was concentrated in vacuo giving 0.84 g of amorphous white solid, m.p. 75°-82° C. $[\alpha]^D{}_{25}=+44.2°$ (C=1.0, $CHCl_3$).

Anal. Calcd. for $C_{23}H_{28}N_2O_5 \cdot 0.8H_2O$: C, 64.72; H, 6.99; N, 6.57. Found: C, 64.41; H, 6.77; N, 7.14.

NMR (DMSO-$d_6$): 1.00 (3, d [7.0 Hz]); 1.13 (3, t [7.4 Hz]); 1.16 (2, m); 2.60 (2, m); 3.19 (2, m); 3.99 (2, q [7.4 Hz]); 4.24 (2, s); 7.19 (5, m); 7.36 (5, m).

IR (KRr): 700, 1215, 1455, 1495, 1595, 1660, 1735, 2940, 2980, 3440 cm$^{-1}$.

EXAMPLES 2-9

Following the procedures given under Example 1, but substituting the dipeptide ester listed in column I for t-butyl N-S-alanyl-N-phenylglycinate, yields the dipeptide derivative listed in column II.

| Example | Column I | Column II |
|---|---|---|
| 2 | N—S—alanyl-N—(2-methylphenyl)-glycinate, t-butyl ester | N—[1-(ethoxycarbonyl)-3-phenylpropyl]alanyl-N—(2-methylphenyl)-glycine |
| 3 | N—S—alanyl-N—(3-chlorophenyl)-glycinate, t-butyl ester | N—[1-(ethoxycarbonyl)-3-phenylpropyl]alanyl-N—(3-chlorophenyl)-glycine. |
| 4 | N—S—alanyl-N—(2-methoxyphenyl)-glycinate, t-butyl ester | N—[1-(ethoxycarbonyl)-3-phenylpropyl]alanyl-N—(2-methoxyphenyl) glycine |
| 5 | N—(S—alanyl)-N—(4-ethylphenyl)-alanate, t-butyl ester | N—[1-(ethoxycarbonyl)-3-phenylpropyl]alanyl-N—(4-ethylphenyl) alanine |
| 6 | N—(S—alanyl)-N—(3-methylphenyl)-2-propylglycinate, t-butyl ester | N—[1-(ethoxycarbonyl)-3-phenylpropyl]alanyl-N—(3-methylphenyl)-2-propylglycine |
| 7 | N—[(2-phenylethyl)glycyl]-N—phenylglycinate, t-butyl ester | N—[1-(ethoxycarbonyl)-2-phenylethyl-3-phenylpropylglycyl]-N—phenylglycine |
| 8 | 1-(S—alanyl)indoline-2-carboxylate, t-butyl ester | 1-(N—[1-ethoxycarbonyl)-3-phenylpropyl]alanyl)indoline-2-carboxylic acid |
| 9 | 1-(S—alanyl)-1,2,3,4-tetrahydroquinoline-2-carboxylate, t-butyl ester | 1-(N—[1-(ethoxycarbonyl)-3-phenylpropyl]alanyl)-1,2,3,4-tetrahydroquinoline-2-carboxylic acid |

What is claimed is:

1. A compound having formula I

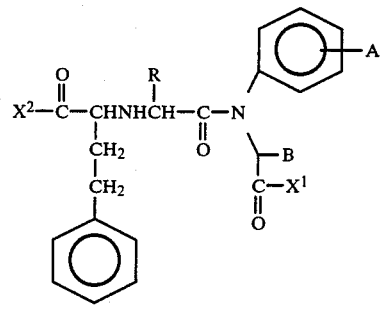

and the non-toxic pharmaceutically acceptable salts thereof wherein
A is hydrogen;
B is hydrogen or lower alkyl;
R is hydrogen, lower alkyl, or phenyl-lower alkyl; and
$X^1$ and $X^2$ are independently selected from hydroxy or lower ($C_1$–$C_4$) alkoxy groups.

2. The compound of claim 1 wherein R is methyl, $X^1$ is hydroxy, and $X^2$ is alkoxy.

3. The compound of claim 1, (S,S)-N-1-(ethoxycarbonyl)-3-phenylpropyl alanyl-N-phenylglycine.

4. A pharmaceutical composition for the treatment of angiotensin-dependent hypertension comprising from 0.1 to 100 mg per kg of body weight per day of a claim 1 compound of formula I or a pharmaceutically acceptable non-toxic salt thereof in combination with a pharmaceutically acceptable, non-toxic inert carrier.

5. The antihypertensive method which comprises administering to a mammalian host having hypertension a non-toxic antihypertensive effective dose of a formula I compound claimed in claim 1.

* * * * *